United States Patent
Packer

(10) Patent No.: US 6,676,680 B1
(45) Date of Patent: Jan. 13, 2004

(54) TAMPONADE DEVICE TO CONTROL POST-PARTUM HEMORRHAGE

(75) Inventor: Paul R. Packer, New Rochelle, NY (US)

(73) Assignee: Polyzen, Inc., Cary, NC (US)

( * ) Notice: Subject to any disclaimer, the term of this patent is extended or adjusted under 35 U.S.C. 154(b) by 3 days.

(21) Appl. No.: 10/179,104

(22) Filed: Jun. 25, 2002

Related U.S. Application Data

(60) Provisional application No. 60/306,531, filed on Jul. 17, 2001.

(51) Int. Cl.[7] ............................................. A61M 29/00
(52) U.S. Cl. ....................................... 606/193; 607/104
(58) Field of Search ................. 606/192, 193, 606/27; 607/104, 105, 113

(56) References Cited

U.S. PATENT DOCUMENTS

| | | | | |
|---|---|---|---|---|
| 3,875,939 A | * | 4/1975 | Bolduc et al. | 606/193 |
| 5,957,962 A | * | 9/1999 | Wallsten et al. | 607/104 |

* cited by examiner

Primary Examiner—Kevin T. Truong
(74) Attorney, Agent, or Firm—Steven J. Hultquist; Marianne Fuierer; Yonqzhi Yang

(57) ABSTRACT

A tamponade device for controlling post-partum hemorrhage includes an inner drain tube co-axially encircled by an inflatable balloon. The device is inserted into the uterine cavity, and the balloon is distended with a medium supplied with sufficient pressure and volume to apply even pressure along the surface of an interior uterine wall. With the application of such pressure, bleeding is stopped as evidenced by a cessation of blood draining from the inner drain tube. The inner tube includes a drainage port at an inserted end for draining blood and other fluids from the interior of the uterine cavity. An integral valve and medium insufflation and supply tubes operate to control inflation and deflation of the balloon. The supply tube co-axially encircles the drain tube to define a thin passageway between an inner surface of the supply tube and an outer surface of the drain tube. Perforations in the supply tube allow the medium to pass from this passageway in order to distend the balloon. The balloon may be coated or impregnated with a hemostatic material in order to further control bleeding.

23 Claims, 2 Drawing Sheets

TAMPONADE DEVICE TO CONTROL POST-PARTUM HEMORRHAGE

CROSS-REFERENCE TO RELATED APPLICATION

The present application claims priority under 35 U.S.C. §119(e) from U.S. Provisional Patent Application No. 60/306,531 for "A DEVICE TO CONTROL POST-PARTUM HEMORRHAGE," filed on Jul. 17, 2001 in the name of Paul R. Packer. U.S. Provisional Patent Application No. 60/306,531 was filed by an inventor common to the present application, and is hereby incorporated by reference.

FIELD OF THE INVENTION

This invention relates to a device for controlling post-partum hemorrhage, and more particularly, to a tamponade device for controlling uterine and vaginal post-partum hemorrhage.

BACKGROUND OF THE INVENTION

Postpartum hemorrhage is most commonly caused by uterine atony whereby the uterus fails to contract normally after the delivery of a baby. This condition occurs in about 5 percent of deliveries. Hemorrhage continues to be one of the major causes of maternal deaths generally, with obstetrical hemorrhage being the third leading cause of maternal death by hemorrhage in the United States. Worldwide, maternal hemorrhage qualifies as the leading cause of maternal death.

Techniques for managing obstetrical hemorrhage may be medical, mechanical, or surgical. Hysterectomy, while an effective surgical procedure for treating this condition, bears severe consequences, in particular for young women who have not completed childbearing.

One of the mechanical procedures often used for managing obstetrical hemorrhage involves packing the uterus with heavy gauze. This procedure remains controversial because of a high failure rate, and is considered a waste of time by some medical practitioners. The high failure rate is attributable to the inherent difficulty in packing the uterus properly so that there is an even distribution of pressure along the entire inner surface of the organ.

Accordingly, a more effective procedure is needed to address post-partum hemorrhage and bleeding. Ideally, the procedure should present minimal long-term health consequences to the patient, be quickly and easily accomplished, be easily learned and require no specialized instrumentation.

U.S. Pat. No. 4,619,261 issued on Jun. 17, 1980 to Guerriero, discloses a hydrostatic pressure application device for controlling bleeding from an internal wound. The device of Guerriero comprises a balloon captured within a net. The net is secured to an area surrounding a wound with surgical sutures, so that hydraulic pressure applied to the balloon expands the balloon and causes pressure to be applied at the wound. Pressure so applied at the wound causes a cessation in bleeding. Disadvantageously, however, because the device is sutured to an area surrounding the wound, applying and removing the device of Guerriero requires an operative (surgical) procedure.

U.S. Pat. No. 4,207,891 issued on Jun. 17, 1980 to Bolduc, discloses a fluid dispensing instrument having a dispenser that operates to place a drug material into a uterine cavity, and an expandable balloon that operates to move the drug material from the uterine cavity into both canals of the Fallopian tubes. However, the dispensing instrument of Bolduc is not configured and operated in a manner directed to the control of post-partum hemorrhage and bleeding.

U.S. patent application Ser. No. US2001/0007945 published on Jul. 12, 2001 to Piraka discloses a uterine balloon for controlling hemorrhaging in a patient after childbirth. The balloon of Piraka is filled with a physiologic solution by means of a catheter inserted through a valve in the balloon. A fill system, a control system, and a pressure relief valve are each employed for maintaining a constant solution pressure in the balloon. However, no means are disclosed for determining whether bleeding has been effectively stopped, in order to adapt balloon pressure accordingly.

None of the above-described devices provide the full advantage of the novel device and method described herein.

SUMMARY OF THE INVENTION

A novel device and method are disclosed for controlling uterine and vaginal post-partum hemorrhage.

The present invention comprises a tamponade device having an inflatable balloon whose shape, when inflated, takes on the shape of the site to be controlled (for example, the shape of a uterine wall). The device also comprises an internal drain tube coaxially and sealably positioned with respect to the balloon, and having a port at an inserted end for draining blood and other fluids from the uterine cavity. An insufflation tube feeds a distending medium (such as air or a physiologic fluid) through a supply tube to inflate the balloon. The supply tube co-axially encircles the drain tube to define a thin passageway between an inner surface of the supply tube and an outer surface of the drain tube. Perforations in the supply tube allow the medium to pass from this passageway in order to distend the balloon.

With sufficient inflation pressure, the balloon exerts a uniform distribution of compressive pressure, which in turn controls bleeding sites. This control of bleeding gives the uterus time to respond normally as bleeding stops, and conserves blood while preparing the patient for surgery as necessary. This device may also be utilized in the vagina to control bleeding associated with submucosal tears (tears under the mucosal vaginal lining), and with any continuous bleeding resulting in the subsequent development of hematomas. Accordingly, significant blood loss, pain, and the possibility of an operative procedure may be prevented. In a preferred embodiment of the present invention, an outer surface of the balloon is coated or impregnated with a hemostatic material for contact with the uterine wall or vaginal lining to provide additional control of bleeding.

An advantage provided by the present invention is that its insertion, inflation, and removal require no surgical procedures, and very little time. The device is thus uniquely and admirably suitable for use in uterine hemorrhaging emergencies. Other presently known devices which use expandable material to stop abdominal bleeding during or after surgery are considerably more complicated in construction and much more difficult to use, often requiring surgical application and removal.

BRIEF DESCRIPTION OF THE DRAWINGS

A more complete understanding of the invention may be obtained by reading the following description of specific illustrative embodiments of the invention in conjunction with the appended drawing in which.

DETAILED DESCRIPTION OF THE PREFERRED EMBODIMENTS

The following detailed description includes a description of the best mode or modes of the invention presently contemplated. Such description is not intended to be understood in a limiting sense, but to be an example of the invention presented solely for illustration thereof, and by reference to which in connection with the following description and the accompanying drawing one skilled in the art may be advised of the advantages and construction of the invention.

Figure 1:
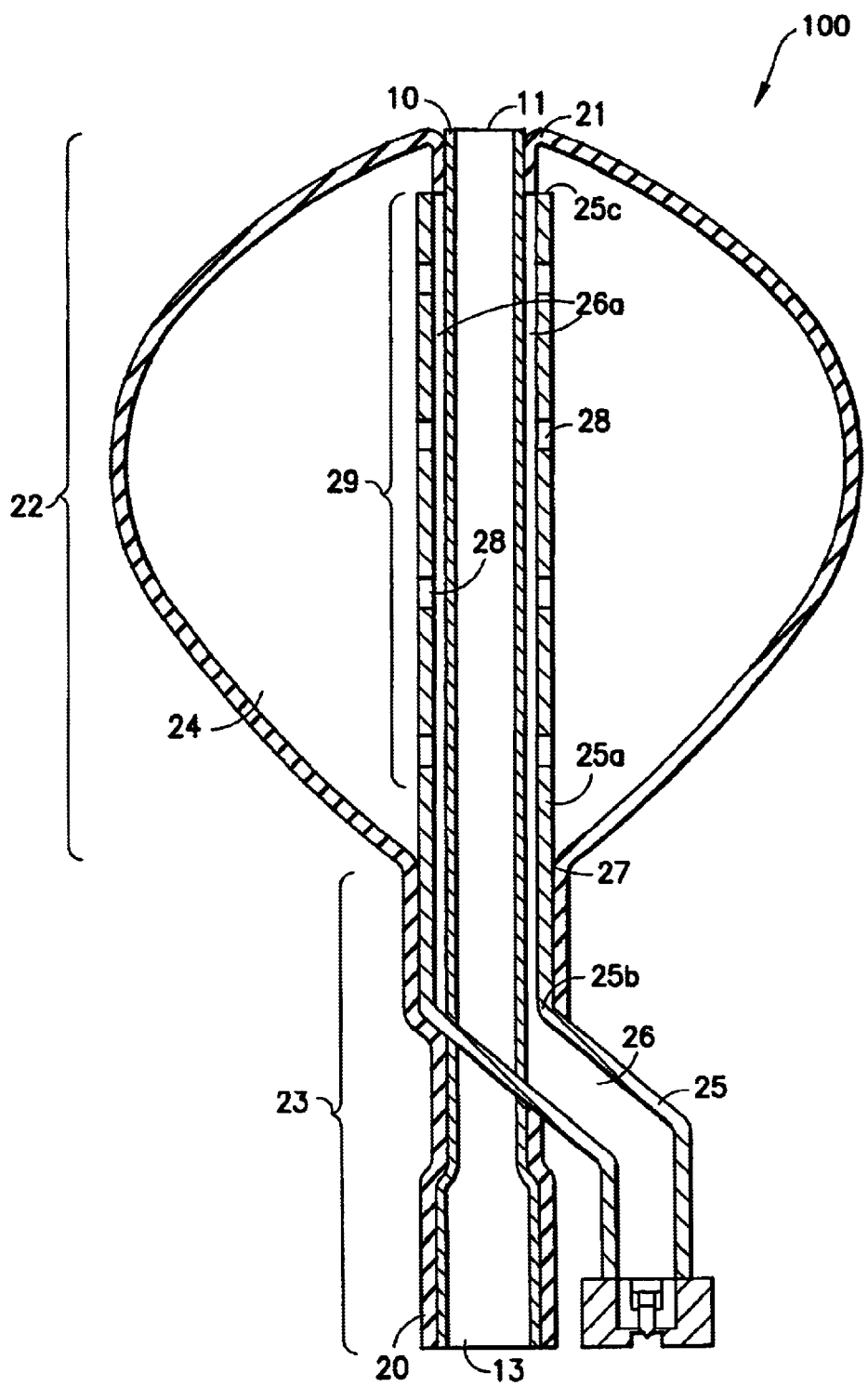
FIG. 1 illustrates a cross-sectional view of a hemorrhage control device according to the present invention.

Referring to the FIG. 1, hemorrhage control device 100 comprises an inner drain tube 10 and an outer sheathing 20. Outer sheathing 20 coaxially surrounds inner drain tube 10 over lengths defined by insertable portion 22 and external portion 23. Over external portion 23, outer sheathing 20 is sealably attached to inner drain tube 10. Over insertable portion 22, outer sheathing 20 comprises a balloon 24 that may be distended with a medium (gas or fluid) via insufflation tube 25 and supply tube 25a to occupy an expanded shape. At one end, balloon 24 meets external portion 23 of sheathing 20 at seal 27. Near an end of insertable portion 22, seal 21 fixedly and sealably joins another end of balloon 24 to inner drain tube 10.

Seals 21, 27 thereby provide means for retaining the distending medium within an interior volume of balloon 24, and for restraining inner drain tube 10 to balloon 24. Insufflation tube 25 sealably surrounds inner drain tube 10 at an end 25b that joins to supply tube 25a. Supply tube 25a co-axially encircles drain tube 10 to define passageway 26a between supply tube 25a and drain tube 10. At end 25b, passageway 26 of insufflation tube 25 couples to passageway 26a of co-axial supply tube 25a for delivering the distending medium to the interior volume of balloon 24 via a plurality of perforations 28 distributed over region 29 of co-axial supply tube 25a. Supply tube 25a and passageway 26a sealably terminate near a terminating end 25c of inner drain tube 10.

As shown in FIG. 1, insufflation tube 25 preferably mates with inflation control valve 30 for maintaining balloon 24 in an inflated state, and for controllably deflating balloon 24 when it is required that pressure supplied to the uterine cavity be reduced or altogether removed. Valve 30 may comprise one of a variety of conventional devices including, for example, ball valves and needle valves. Valve 30 may alternatively comprise a connecting area (for example, using a glass adapter) for connecting a fluid tube to insufflation tube 25.

Balloon 24 is made of an expandable material, such as urethane, natural rubber, silicone, synthetic rubber or vinyl, and may preferably be inflated hold up to 4000 cubic centimeters (cc) of air volume. Balloon 24 is also preferably heart-shaped when inflated so that it will evenly conform, for example, to the interior surface of the uterine wall. Conformance of the exterior shape of balloon 24 with the interior shape of the uterine wall enables balloon 24 to fit evenly and tightly against this surface, thereby providing pressure against all associated bleeding sites.

An external surface of balloon 24 may preferably be coated, impregnated or otherwise covered with a hemostatic material in order that this hemostatic material may come into direct contact with the uterine wall or vaginal lining to further assist in controlling bleeding. Oxidized cellulose and hemotene are materials suitably used for this purpose.

Inner drain tube 10, outer sheathing 20 and insufflation tubes 25, and supply tube 25a may also be made from a flexible material such as neoprene, natural rubber, silicone, synthetic rubber or vinyl. Inner drain tube 10 however must be sufficiently rigid to maintain its inner diameter when balloon 24 is inflated, and therefore may either be made from a more rigid material than balloon 24 or have a thicker cross-section than balloon 24.

As illustrated by FIG. 1, inner drain tube 10 has a drainage port 11 at its distal end for receiving blood and other fluids to be drained from the uterine cavity. Without adequate drainage, bleeding may continue unobserved in spite of the pressure applied by balloon 24, and may possibly lead to severe bleeding diathasis. At an end of external portion 23, inner drain tube 10 may optionally include expanded portion 13 for coupling inner drain tube 10 to another vessel having, for example, a passageway of like inner diameter to inner drain tube 10. Inner drain tube 10 may also be used, for example, to irrigate the uterus as necessary by introducing irrigation fluids at expanded portion 13.

Hemorrhage control device 100 of FIG. 1 may be simply operated by inserting the device 100 to a desired position in the uterine cavity and inflating balloon 24 to a desired pressure and volume. Optimum pressure is detected, for example, when there is no further fluid drainage. After an appropriate length of time, pressure can be lowered and observations made to determine whether or not bleeding has been controlled, and to determine whether the uterus is showing signs of contracting normally. If bleeding begins again or the uterus remains soft and boggy, the balloon may be re-inflated.

When the device is used to stop bleeding in the vagina due to submucosal tears, it will require a much smaller volume of gas or fluid for balloon 24 to accommodate itself to the shape of the vagina. Optimally formed balloon shapes and sizes in either uterine or vaginal applications will vary with patient anatomy. Accordingly, a variety of balloon shapes and sizes may be employed in the present invention, each of which is fully contemplated within the scope of the present invention.

A variety of gases (for example, air) and fluids may be used to inflate balloon 24 of FIG. 1. In a preferred embodiment of the present invention, a fluid comprising a normal saline solution is used to inflate the balloon. Fluid media have an advantage over gaseous media in decreasing the risk of generating embolisms.

Figure 2:
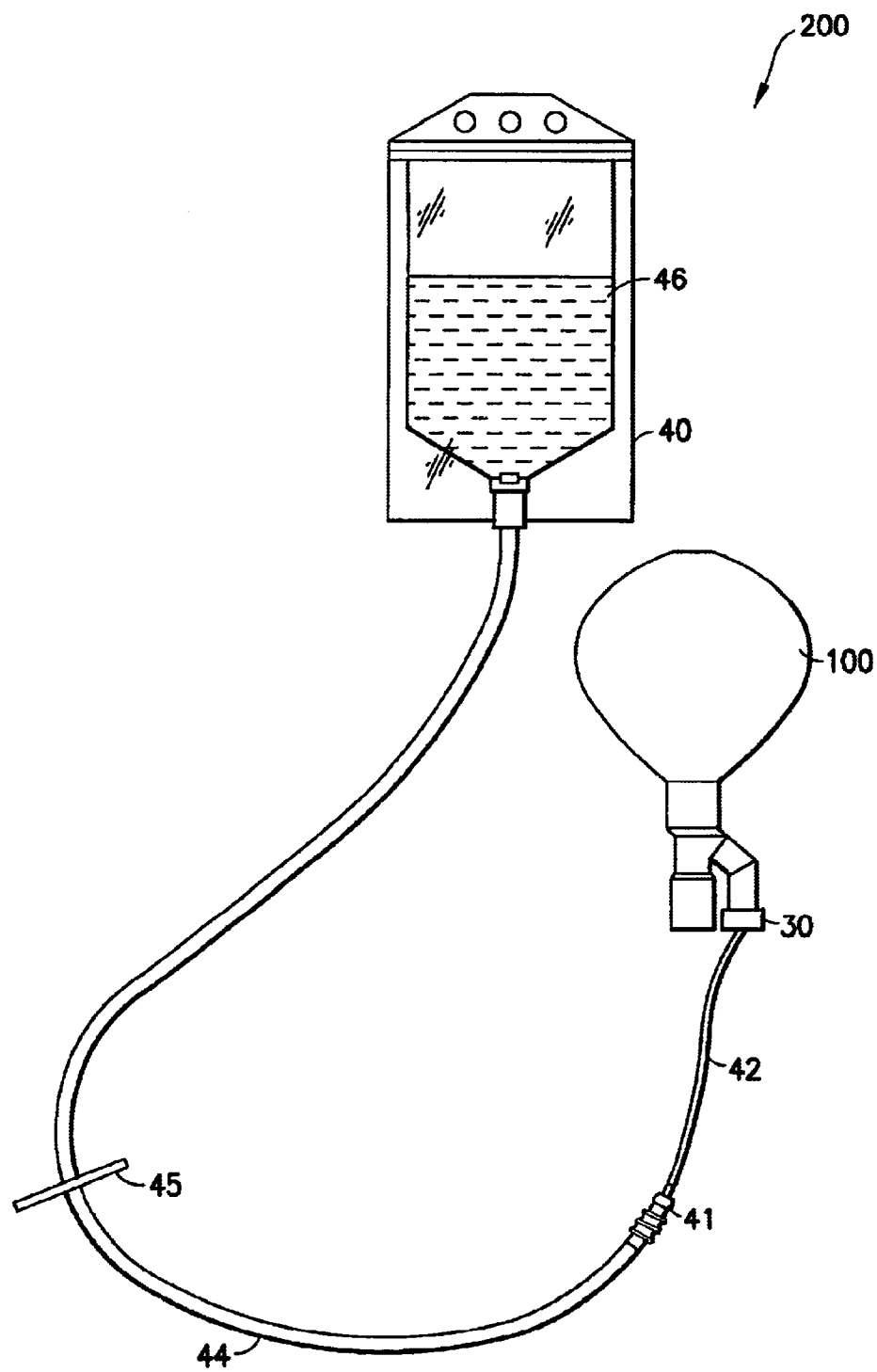
FIG. 2 illustrates a mechanism for supplying fluid to fill a balloon of the hemorrhage control device.

FIG. 2 illustrates an apparatus 200 for supplying a fluid medium to the hemorrhage control device 100. In the apparatus 200, intravenous (IV) bag 40 contains a saline solution 46. Bag 40 may be hung approximately three to four feet above a position of hemorrhage control device 100 in order to provide sufficient supply pressure for inflating balloon 24 of hemorrhage control device 100 to curtail bleeding. Adapter 41 may be used to couple tube 44 to coupling tube 42, and thereby to valve 30 of hemorrhage control device 100. Hemostat 45 may be used to clamp tube 44 for controlling the flow of saline solution 46 into the balloon of hemorrhage control device 100. When it is desired to reduce pressure or volume of the balloon, tube 44 may be disconnected at adapter 41, and coupling tube 42 positioned so that fluid is able to drain from device 100 by gravity flow.

While the present invention has been described at some length and with some particularity with respect to the several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope of the invention.

I claim:

1. A device for controlling post-partum hemorrhage, the device comprising:
   an inner drain tube having a passage with openings at opposing ends for draining fluid from at least one of a uterine cavity and a vaginal area; and
   an outer sheath coaxially positioned over the inner drain tube, the outer sheath further comprising a balloon surrounding a portion of the drain tube, said balloon being inflatable to apply a substantially even pressure along a substantial portion of at least one of a vaginal wall and an inner uterine wall for controlling bleeding sites along said substantial portion.

2. The device of claim 1, further comprising an insufflation means that communicates with the balloon for introducing and removing an externally supplied medium comprising at least one of a gas and a fluid in the balloon.

3. The device of claim 2, wherein the medium is air.

4. The device of claim 2, wherein the medium is a saline solution.

5. The device of claim 4, wherein the medium is a normal saline solution.

6. The device of claim 2, wherein the insufflation means comprises: an insufflation tube for receiving the externally supplied medium; and a supply tube that communicates with the insufflation tube and balloon.

7. The device of claim 6, wherein the supply tube is fixedly and co-axially inserted between the sheath and the inner drain tube, and defines a passageway between the supply tube and the inner drain tube for supplying the medium to the balloon.

8. The device of claim 7, wherein the supply tube further includes one or more perforations for transferring the medium from the passageway to an interior of the balloon.

9. The device of claim 2, wherein the insufflation means further includes a valve for controlling the introduction and removal of said medium.

10. The device of claim 9, wherein the valve comprises one of a ball valve, a needle valve and a clamp.

11. The device of claim 1, wherein the balloon has an inflated shape that naturally conforms to at least one of the vaginal wall and the inner uterine wall.

12. The device of claim 11, wherein the conforming shape is a heart shape.

13. The device of claim 12, wherein the balloon is inflatable to hold at least 4000 cubic centimeters (cc) of a distending medium.

14. The device of claim 12, wherein the balloon is inflatable to reach a length of about 16 centimeters (cm).

15. The device of claim 1, wherein the balloon comprises a material selected from the group consisting of urethane, neoprene, vinyl, natural rubber, silicone and synthetic rubber.

16. The device of claim 1, wherein the balloon further comprises a hemostatic material located on an outer surface of the balloon.

17. The device of claim 16, wherein the hemostatic material comprises at least one of oxidized cellulose and hemotene.

18. The device of claim 16, wherein the hemostatic material is impregnated in the outer surface of the balloon.

19. A method for controlling post-partum hemorrhage, the method comprising the steps of:
   providing a drain tube having a passage with openings at opposing ends for drawing fluids from at least one of a uterine cavity and a vaginal cavity;
   sealably surrounding a portion of the drain tube with a balloon;
   inserting the drain tube into at least one of an internal uterine wall area and a vaginal wall area; and
   inflating the balloon with a medium in order to distend the balloon for applying a substantially even pressure over the at least one wall area.

20. The method of claim 19, wherein the medium is air.

21. The method of claim 19, wherein the medium comprises a saline solution.

22. The method of claim 19, wherein the substantially even pressure is applied to an interior uterine wall surface; further comprising the step of:
   deflating the balloon in order to decrease balloon pressure in response to a contraction of the uterus.

23. The method of claim 22, further comprising the steps of:
   reinflating the balloon to increase the balloon pressure when continued bleeding is evident at the drain tube.

* * * * *

UNITED STATES PATENT AND TRADEMARK OFFICE
CERTIFICATE OF CORRECTION

PATENT NO. : 6,676,680 B1
DATED : January 13, 2004
INVENTOR(S) : Packer, Paul R.

It is certified that error appears in the above-identified patent and that said Letters Patent is hereby corrected as shown below:

Column 1,
Line 67, "Fallopian" should be -- fallopian --

Column 2,
Line 3, "patent application" should be -- Patent Application --

Column 3,
Line 52, "inflated hold" should be -- inflated to hold --

Signed and Sealed this

Twenty-third Day of March, 2004

JON W. DUDAS
*Acting Director of the United States Patent and Trademark Office*